United States Patent
Thiruvenkadam et al.

(10) Patent No.: US 8,569,706 B2
(45) Date of Patent: Oct. 29, 2013

(54) METHOD AND SYSTEM FOR PROCESSING GATED IMAGE DATA

(75) Inventors: Sheshadri Thiruvenkadam, Bangalore (IN); Rakesh Mullick, Bangalore (IN); Kris Filip Johan Jules Thielemans, London (GB); Srikrishnan Viswanathan, Kamataka (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/487,046

(22) Filed: Jun. 1, 2012

(65) Prior Publication Data

US 2012/0305780 A1    Dec. 6, 2012

(30) Foreign Application Priority Data

Jun. 3, 2011    (IN) .......................... 1890/CHE/2011

(51) Int. Cl.
*G01T 1/164*    (2006.01)
(52) U.S. Cl.
USPC ................................... 250/363.03
(58) Field of Classification Search
USPC .................. 250/363.01–363.1, 362
See application file for complete search history.

(56) References Cited

U.S. PATENT DOCUMENTS

| | | | |
|---|---|---|---|
| 7,359,535 B2 | 4/2008 | Salla | |
| 7,787,675 B2 | 8/2010 | Pan | |
| 2005/0123183 A1 | 6/2005 | Schleyer | |
| 2010/0046821 A1 | 2/2010 | Manjeshwar | |
| 2010/0310140 A1 | 12/2010 | Schneider | |

FOREIGN PATENT DOCUMENTS

WO    2006119623 A1    11/2006

OTHER PUBLICATIONS

Ishikawa et al., "Retrospective resiratory motion compensation under deep breathing in spiral transmission scanning of 3D PET," 2006, IEEE Nuclear Science Symposium Conference Record, vol. M11-322, pp. 2727-2730.*
Dawood et al., "Respiratory Motion Correction on 3D Positron Emission Tomography Images", 2008.
Langer., "Event-Driven Motion Compensation in Position Emission Tomography: Development of a Clinically Applicable Method", Technische Universitat Dresden, 2008.
Dawood et al., "Respiratory Motion Correction in 3D PET Data with Advanced Optical Flow Algorithms", IEEE Transaction on Medical Imaging, 2008.
Ali et al., "An Algorithm to Extract Three-Dimensional Motion by Marker Tracking in the kV Projections from an On-Board Imager: Four-Dimensional Cone-Beam CT and Tumor Tracking Implications", Journal of Applied Clinical Medical Physics, vol. 12, Issue 2, 2011.

(Continued)

*Primary Examiner* — Kiho Kim
(74) *Attorney, Agent, or Firm* — Global Patent Operation; Mark A. Conklin

(57) ABSTRACT

A method for generating an image is provided. The method comprises: acquiring a first set of image data using a first imaging modality; sorting the first set of image data into a plurality of gates to generate a plurality of gated data sets; reconstructing each gated data set to generate a respective gated image for each gated data set; registering the respective gated images to generate a plurality of registered images; and generating a median image from the plurality of registered images, wherein each voxel of the median image is a respective median value of the corresponding voxels of the plurality of registered images.

20 Claims, 7 Drawing Sheets

(56) References Cited

OTHER PUBLICATIONS

Nestares et al., "Robust Multiresolution Alignment of MRI Brain Volumes", Magnetic Resonance in Medicine, vol. 43, pp. 705-715, 2000.

Hellier et al., "Hierarchical Estimation of a Dense Deformation Field for 3-D Robust Registration", IEEE Transactions on Medical Imaging, vol. 20, No. 5, pp. 388-402, May 2001.

* cited by examiner

METHOD AND SYSTEM FOR PROCESSING GATED IMAGE DATA

BACKGROUND OF THE INVENTION

1. Field of the Invention

Embodiments of the invention relate to algorithms for the processing of acquired image data and the reconstruction of images from data collected using an imaging modality and, more particularly, to imaging modalities such as a PET or SPECT imaging modality, a computed tomography (CT) or magnetic resonance imaging (MRI) imaging modality, and a combined imaging modality, such as a PET/CT or SPECT/CT imaging system.

2. Description of Related Art

In positron emission tomography (PET) imaging and single positron emission computed tomography (SPECT) imaging, a radiopharmaceutical is administered to a patient. The radiopharmaceutical is typically selected so as to be preferentially or differentially distributed in the body based on the physiological or biochemical processes in the body. For example, a radiopharmaceutical may be selected that is preferentially processed or taken up by tumor tissue. In such an example, the radiopharmaceutical will typically be disposed in greater concentrations around tumor tissue within the patient.

In the context of PET imaging, the radiopharmaceutical typically breaks down or decays within the patient, releasing a pair of gamma rays moving in opposite directions in the process. In SPECT imaging, a single gamma ray is generated when the radiopharmaceutical breaks down or decays within the patient. These gamma rays interact with detection mechanisms within the respective PET or SPECT scanner, which allow the decay events to be localized, thereby providing a view of where the radiopharmaceutical is distributed throughout the patient. In this manner, a caregiver can visualize where in the patient the radiopharmaceutical is disproportionately distributed and may thereby identify where physiological structures and/or biochemical processes of diagnostic significance are located within the patient.

The PET or SPECT examination may be conducted over a relatively lengthy time interval, such as over the course of twenty-five to thirty minutes. That is, the decay process associated with the radiopharmaceutical may take place over a period of time, during which measurements are collected and during which the patient must remain relatively still. However, it may be difficult for a patient to remain perfectly still over the period of time involved in such an examination. Further, even discounting the voluntary or controllable motions a patient may perform, various physiological processes, such as the patient's respiration and/or heartbeat, necessarily introduce motion into the examination process over the time interval in question. Such motion (voluntary or otherwise) can lead to artifacts and/or other discrepancies in the resulting visualizations, which may reduce or limit the ability of a caregiver or other medical professional to isolate the locations or locations of interest in a patient where the radiopharmaceutical is aggregated.

BRIEF DESCRIPTION OF THE INVENTION

According to an embodiment of the present invention, a method for generating an image is provided. The method comprises: acquiring a first set of image data using a first imaging modality; sorting the first set of image data into a plurality of gates to generate a plurality of gated data sets; reconstructing each gated data set to generate a respective gated image for each gated data set; registering the respective gated images to generate a plurality of registered images; and generating a median image from the plurality of registered images. Each voxel of the median image is a respective median value of the corresponding voxels of the plurality of registered images.

According to another embodiment of the present invention, one or more non-transitory computer-readable media, encoding one or more routines which, when executed by a processor, cause the processor to perform acts, are provided. The acts comprise: acquiring a first set of image data using a first imaging modality; sorting the first set of image data into a plurality of gates to generate a plurality of gated data sets; reconstructing each gated data set to generate a respective gated image for each gated data set; registering the respective gated images to generate a plurality of registered images; and generating a median image from the plurality of registered images, wherein each voxel of the median image is a respective median value of the corresponding voxels of the plurality of registered images.

According to another embodiment of the present invention, an image processing system is provided. The image processing system comprises a memory storing one or more routines, and a processing component configured to execute the one or more routines stored in the memory. When executed by the processing component, the one or more routines: acquire a first set of image data using a first imaging modality; sort the first set of image data into a plurality of gates to generate a plurality of gated data sets; reconstruct each gated data set to generate a respective gated image for each gated data set; register the respective gated images to generate a plurality of registered images; and generate a median image from the plurality of registered images, wherein each voxel of the median image is a respective median value of the corresponding voxels of the plurality of registered images.

According to another embodiment of the present invention, a method for generating an image is provided. The method comprises: acquiring a first set of image data using an imaging modality; sorting the first set of image data into a plurality of gates to generate a plurality of gated data sets; reconstructing each gated data set to generate a respective gated image for each gated data set; registering the respective gated images to generate a plurality of registered images; and generating an average image or a weighted average image from the plurality of registered images. The average image or the weighted average image is generated using a motion-dependent estimator that is statistically robust with respect to outlying data.

According to another embodiment of the present invention, a method for generating an image is provided. The method comprises: acquiring a first set of image data using an imaging modality; sorting the first set of image data into a plurality of gates to generate a plurality of gated data sets; reconstructing each gated data set to generate a respective gated image for each gated data set; registering the respective gated images to generate a plurality of registered images; and generating an average image or a weighted average image from the plurality of registered images. The average image or the weighted average image is generated using an estimator that identifies outliers in the plurality of registered images and discards or downweights the identified outliers.

BRIEF DESCRIPTION OF THE DRAWINGS

Other objects, features and advantages of the embodiments of the present invention will appear on reading the following description, given only as a non-limiting example, and made with reference to the appended drawings in which.

DETAILED DESCRIPTION

According to an embodiment, the acquired image data is gated such that image data acquired during like periods of motion or like time intervals is binned together (for example, based on time/phase or displacement information). Images may be reconstructed from the acquired image data, and the reconstructed images may be registered to a reference image. In certain embodiments the registered images may be averaged, while in other embodiments a median image may be determined for the registered images. In implementations in which the median image is determined, the effects of outlying values on the calculated median image are negligible due to the manner in which a median value is calculated (i.e., by ranking the measured values and designating the centermost measurement or the average of the two centermost measurements as the median value). Based on these approaches, an output image is generated that has better noise properties than in instances where a single gate is employed.

In other embodiments, steps may be employed to address the presence of outlying data measurements, which may be erroneous and/or which may distort the image registration process or cause the registration process to fail. In one such embodiment, data outliers may be identified and excluded, such as by operation of an automated algorithm. In other embodiments, a suitable cost function may be utilized to handle the processing of outlying values so as to arrive at a suitable balance of useful data measurements relative to exclusion of measurements that may impede the registration process and the generation of a useful output image.

Figure 1:
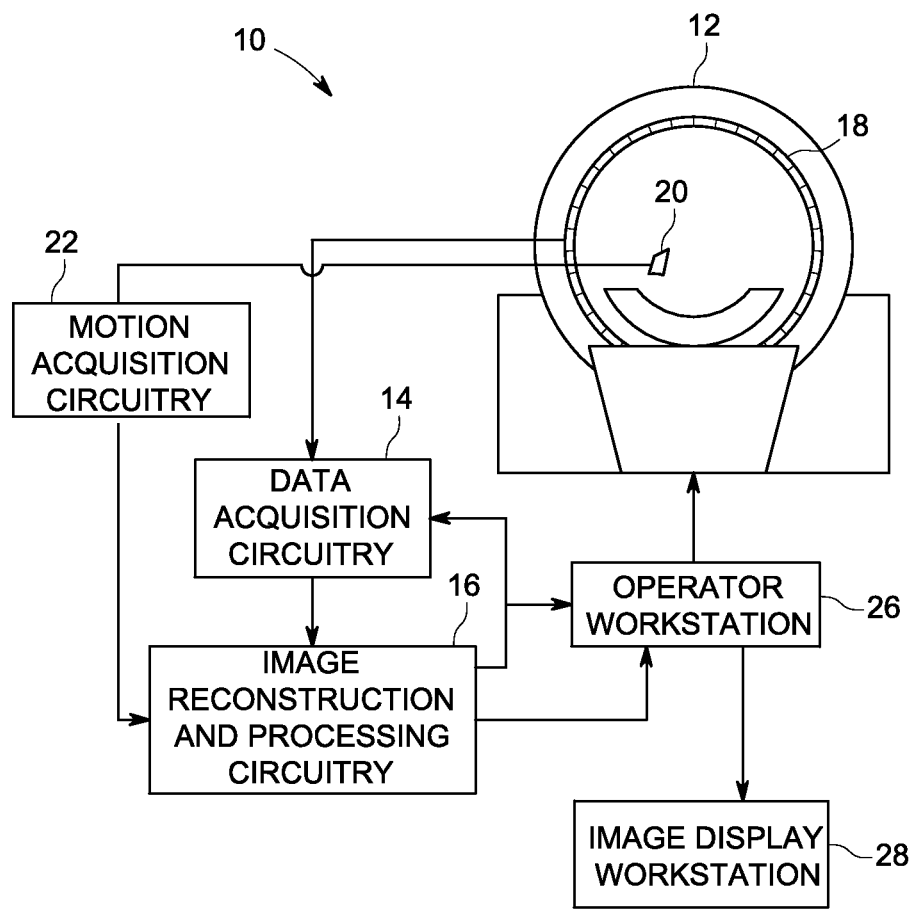
FIG. 1 is a diagrammatical representation of a PET imaging system in accordance with aspects of the present disclosure.

With the foregoing in mind and turning now to the drawings, FIG. 1 depicts a PET or SPECT system 10 operating in accordance with certain aspects of the present disclosure. As will be appreciated, in other implementations a respective imaging system may correspond to another type of imaging modality, such as a CT or MRI imaging system. The PET or SPECT imaging system of FIG. 1 is merely depicted and discussed to facilitate explanation of the presently disclosed image processing approach in a particular context so that aspects of the approach may be more readily appreciated.

Returning now to FIG. 1, the depicted PET or SPECT system 10 includes a detector assembly 12, data acquisition circuitry 14, and image reconstruction and processing circuitry 16. The detector assembly 12 of the PET or SPECT system 10 typically includes a number of detector modules (generally designated by reference numeral 18) arranged about the imaging volume, as depicted in FIG. 1. The depicted PET or SPECT system 10 also includes an operator workstation 26 and an image display workstation 28.

In addition, in accordance with one embodiment, a motion sensor 20 (e.g., a motion tracker) and motion acquisition circuitry 22 are depicted. In one such embodiment, the motion sensor 20 and the motion acquisition circuitry 22 may be provided as separate from the PET or SPECT system 10, such as an electrocardiograph (or other electrical mechanisms for monitoring cardiac and/or respiratory motion), a respiration circuit including a flow gauge or meter suitable for monitoring respiration, and/or one or more accelerometers, strain gauges, or pressure sensors suitable for monitoring respiration and/or cardiac motion. In other embodiments, the motion acquisition circuitry 22 may monitor a cardiac and/or respiratory state of a patient using raw or processed image data, such as may be provided by the PET or SPECT system 10 or by a separate imaging modality (such as by computed tomography (CT) or other X-ray based imaging modalities or by visible-light or infrared cameras) used in conjunction with the PET or SPECT system 10.

To facilitate explanation and discussion of the operation of the PET or SPECT system 10, the detector acquisition circuitry 14, and the image reconstruction and processing circuitry 16 are shown separately from other illustrated components (e.g., the detector assembly 12, the operator workstation 26, and the image display workstation 28). However, in certain implementations, some or all of these circuitries may be provided as part of the detector assembly 12, the operator workstation 26, and/or the image display workstation 28. For example, the hardware, software, and/or firmware executed on or provided as part of the image reconstruction and processing circuitry 16, whether provided as part of the detector assembly 12, the operator workstation 26, and/or the image display workstation 28, may be used to perform various image processing actions described herein. In certain implementations the image reconstruction and processing circuitry 16 may include specially programmed hardware, memory, or processors (e.g., application-specific integrated circuits (ASICs)) for performing image processing steps (e.g., image data gating, image registration, calculation of average and/or median, voxel values, motion estimation, cost function optimization, and so forth) as discussed herein. Similarly, all or part of these image processing steps may be performed using one or more general or special purpose processors and stored code or algorithms configured to execute on such processors. Likewise, a combination of special purpose hardware and/or circuitry may be used in conjunction with one or more processors configured to execute stored code to implement the steps discussed herein. The results of such image processing steps may be displayed on one or both of the operator workstation 26 or a separate image display workstation 28, if present.

Keeping in mind the example of the PET or SPECT system 10 discussed above, or the corresponding components of other types of suitable imaging systems, a brief description of one example of such system is provided to facilitate further explanation of the present approach. By way of example, PET imaging is primarily used to measure metabolic activities that occur in tissues and organs and, in particular, to localize aberrant metabolic activity. In PET imaging, the patient is typically injected with a solution that contains a radioactive tracer. The solution is distributed and absorbed throughout the body in different degrees, depending on the tracer employed and the functioning of the organs and tissues. For instance, tumors typically process more glucose than a healthy tissue of the same type. Therefore, a glucose solution containing a radioactive tracer may be disproportionately metabolized by a tumor, allowing the tumor to be located and visualized by the radioactive emissions. In particular, the radioactive tracer emits positrons that interact with and annihilate complementary electrons to generate pairs of gamma rays. In each annihilation reaction, two gamma rays traveling in opposite directions are emitted. In a PET imaging system 10, the pair of gamma rays are detected by the detector assembly 12 configured to ascertain that two gamma rays detected sufficiently close in time are generated by the same annihilation reaction. Due to the nature of the annihilation reaction, the detection of such a pair of gamma rays may be used to determine the line of response along which the gamma rays traveled before impacting the detector, allowing localization of the annihilation event to that line. By detecting a number of such gamma ray pairs, and calculating the corresponding lines traveled by these pairs, the concentration of the radioactive tracer in different parts of the body may be estimated and a tumor, thereby, may be detected. Therefore, accurate detection and localization of the gamma rays forms a fundamental and foremost objective of the PET system 10.

In view of these comments, and returning now to FIG. 1, the detector acquisition circuitry 14 is adapted to read out signals generated in response to the gamma rays from the detector modules 18 of the detector assembly 12. The signals acquired by the detector acquisition circuitry 14 are provided to the image reconstruction and processing circuitry 16. The image reconstruction and processing circuitry generates an image based on the derived gamma ray emission locations. The operator workstation 20 is utilized by a system operator to provide control instructions to some or all of the described components and for configuring the various operating parameters that aid in data acquisition and image generation. The operator workstation 20 may also display the generated image. Alternatively, the generated image may be displayed at a remote viewing workstation, such as the image display workstation 28.

In certain instances the region of interest for which images are being generated may be subject to motion, either voluntary or involuntary. For example, images generated near the heart and/or lungs may be subject to respiratory and/or cardiac motion effects. Such motion may negatively impact the diagnostic value of images generated for these regions. Likewise, image data outliers due to motion and/or other image acquisition artifacts, such as due to attenuation mismatch and/or scatter estimation issues, may prevent proper registration of the aberrant image data and result in errors being introduced by the registration step. In certain implementations, data related to physiological events resulting in motion, as may be acquired by the motion acquisition circuitry 22, may also be provided to the image reconstruction and processing circuitry 16 to perform motion compensation, correction, or identification. Examples of such approaches are discussed in U.S. patent application Ser. No. 12/873,039, entitled "MOTION COMPENSATION IN IMAGE PROCESSING", filed Aug. 31, 2010, which is herein incorporated by reference in its entirety for all purposes. Further, in certain embodiments, outlying or aberrant data measurements may be addressed by use of a median voxel or image calculation that is robust with respect to such outlying events and/or by use of a suitable cost function used in an image optimization process.

In other instances, the localization and/or observed level of gamma ray emissions is expected to vary over time, such as due to physiological processes (e.g., metabolic processes) and/or the decay rate of the radiological agent. In such dynamic scenarios, a time model describing the kinetic behavior of the injected or ingested agent may be used in assessing measurements acquired over time relative to the model. In such implementations, motion may be a factor. Therefore, in certain embodiments, data related to physiological events resulting in motion may be similarly provided to the image reconstruction and processing circuitry when generating the dynamic images.

Figure 2:
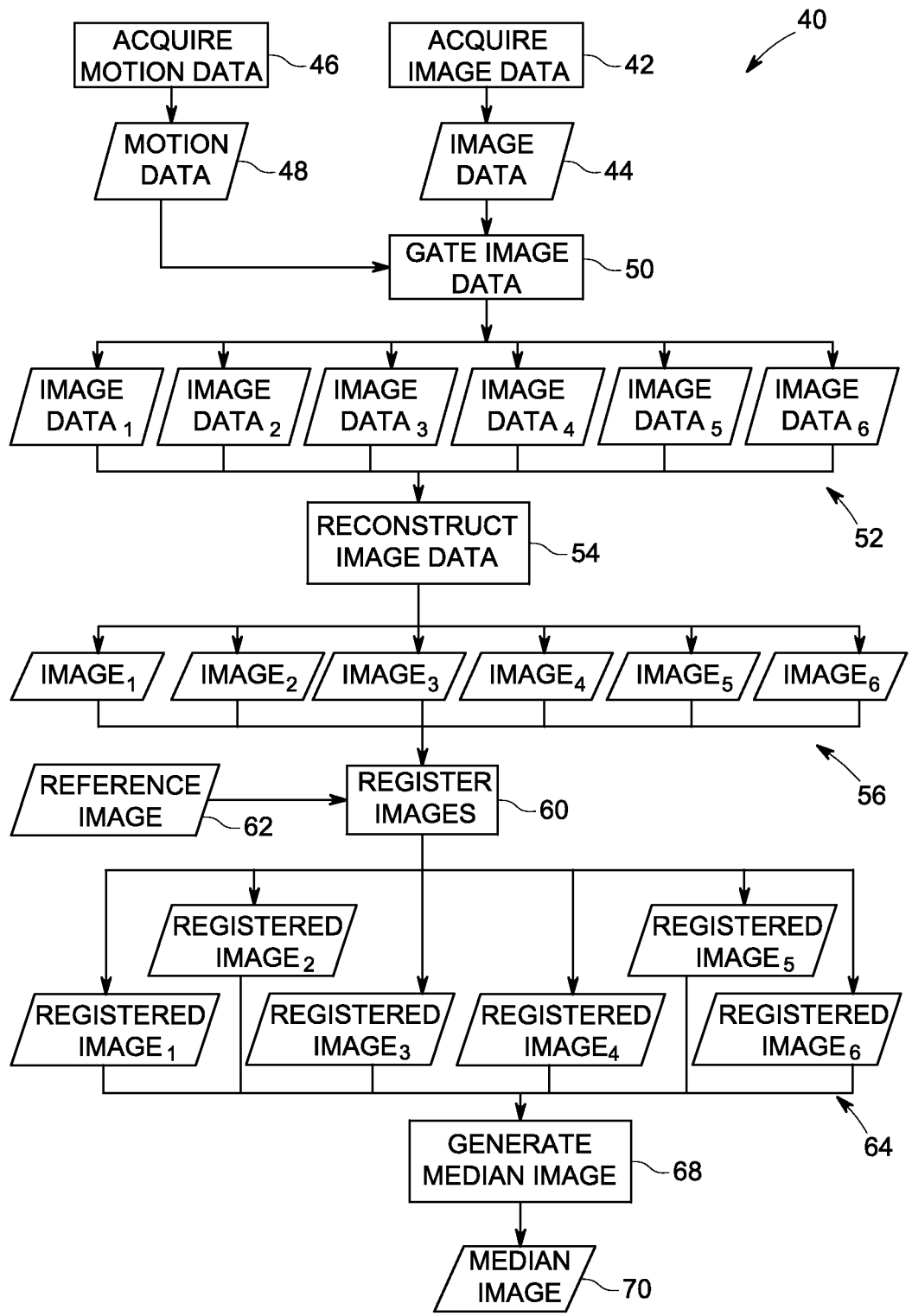
FIG. 2 is a flowchart depicting a method for image processing used to generate a median image in accordance with one embodiment of the present disclosure.

Turning to FIG. 2, an example of a method 40 for generating an image using an imaging system, such as that depicted in FIG. 1, is provided. In accordance with this example, a method 40 is depicted for identifying or compensating for differences in image data, such as due to patient motion is described. In accordance with this example, a set of image data 44 is generated (block 42) or otherwise acquired. In one embodiment, a set of corresponding motion data 48, such as respiratory or cardiac motion data, is acquired (block 46) in conjunction with the image data 44. In the depicted example, a set of motion data 48 is used to gate (block 50) or bin the image data 44 into different phases of like data, e.g., gated data 52. In other embodiments, motion data 48 may be absent and the image data 44 may instead be gated based on the time index or interval associated with the acquisition process. For example, in such an embodiment, each gate or bin may contain the data acquired over a two-minute interval such that, during a ten-minute examination, five two-minute gates may be generated, one for each sequential two-minute interval of the examination.

Regardless of whether the gating process is based on motion, time, or motion and time, the gated image data 52 may be processed to generate (block 54) respective images 56 corresponding to each respective gate. That is, the gated image data 52 associated with each gate is reconstructed to generate a respective image 56 corresponding to the respective gate. Once the gated images 56 are generated, these gated images 56 are registered (block 60) to one another or to one or more specified reference images 62, such as using a reference-based deformable registration process. The registration process may be rigid or non-rigid and acts to transform each registered image 64, based on identified or segmented features, to correspond to a reference image 62 having the same features. Though depicted separately in the figures to facilitate explanation, in certain embodiments the reference image 62 may be one of the registered images 64 or the sum of some or all of the registered images 64. In other embodiments the reference image 62 may be a standardized image, such as an image from an atlas or generated using a kinetic model, or a structural image acquired via other techniques, such as computed tomography (CT) or magnetic resonance imaging (MRI).

In certain implementations where a second imaging modality is present (such as a PET/CT or PET/MRI where the two imaging modalities are provided in a combined system or as separate and distinct imaging modalities) the data acquired by both modalities may be separately gated such that the motion between gates corresponds for each modality. For example, in one embodiment where a first modality is a PET system and where the second modality is a CT or MRI system, the data acquired by both the PET and CT or MRI systems may be gated such that the gated data sets for both modalities include data subject to corresponding motion. In one such implementation, both data sets may be gated based on time index such that the same time indexed data is assigned or sorted into corresponding gates for the separate data sets. The respective number of gates for the data acquired by the different imaging modalities may be the same or different. In instances where the number of gates differ with respect to the data acquired by the different imaging modalities, a motion model may be derived using the data acquired by one modality (such as a CT system) and the derived motion model may then be fit to the gated data acquired by the other modality (such as a PET system).

In one such embodiment, the second set of gated image data (e.g., the CT or MRI image data in the above example) may be reconstructed to generate respective gated images that are registered to derive the respective motion fields for each gated image, as discussed herein with respect to the primary image data set (e.g., the PET image data in the above example). The motion fields derived by registering the gated images of the second modality (e.g., CT or MRI) may then be used to correct for motion in the gated primary modality (e.g., PET) image data. Such an approach of using data acquired by a second image modality to derive motion fields used to further process image data acquired by a first modality may be employed with each of the various approaches discussed herein. That is, to the extent that the derivation or use of motion data or motion fields is discussed herein (such as to correct for motion, perform registration of gated images, and/or identify outliers), the motion data or fields may be derived from image data acquired by either a primary image modality for which the image data is being reconstructed or from the image data acquired by a secondary image modality.

The registration process 60 generates a set of registered images 64 which correspond to the gated images 56 after transformation to correspond to the respective reference image or images. In the depicted example, the registered images 64 may be used to generate (block 68) a median image 70. For example, in an embodiment in which a median image 70 is generated, the median image 70 may be computed over gates at (at every voxel) in accordance with:

$$I_v^{Median} = \text{median}(r_1, r_2, \ldots, t_{N_v}) \quad (1)$$

where $I_v^{Median}$ is the median image, $r_g$ are the registered images, N is the number of gates, and v is the voxel index. That is, the median image 70 at each respective voxel index is computed by ordering the data for all gates and choosing the central point as the voxel value. In instances where there is an even number of data points, the average of the two most central points may be used as the central point. In this manner, a median image 70 may be generated in which the value at each voxel is the median value for that voxel across gates as determined from the registered images. As will be appreciated, the median operation reduces or eliminates the effect of outlying data points and does not require that any parameters be specified. Further, in a statistical sense, the breakdown point of the median is 50%, which means that nearly half the observations could be potentially corrupted before the median estimate breaks down. Once generated, the median image 70 may be viewed by trained personnel for evaluation.

Figure 3:
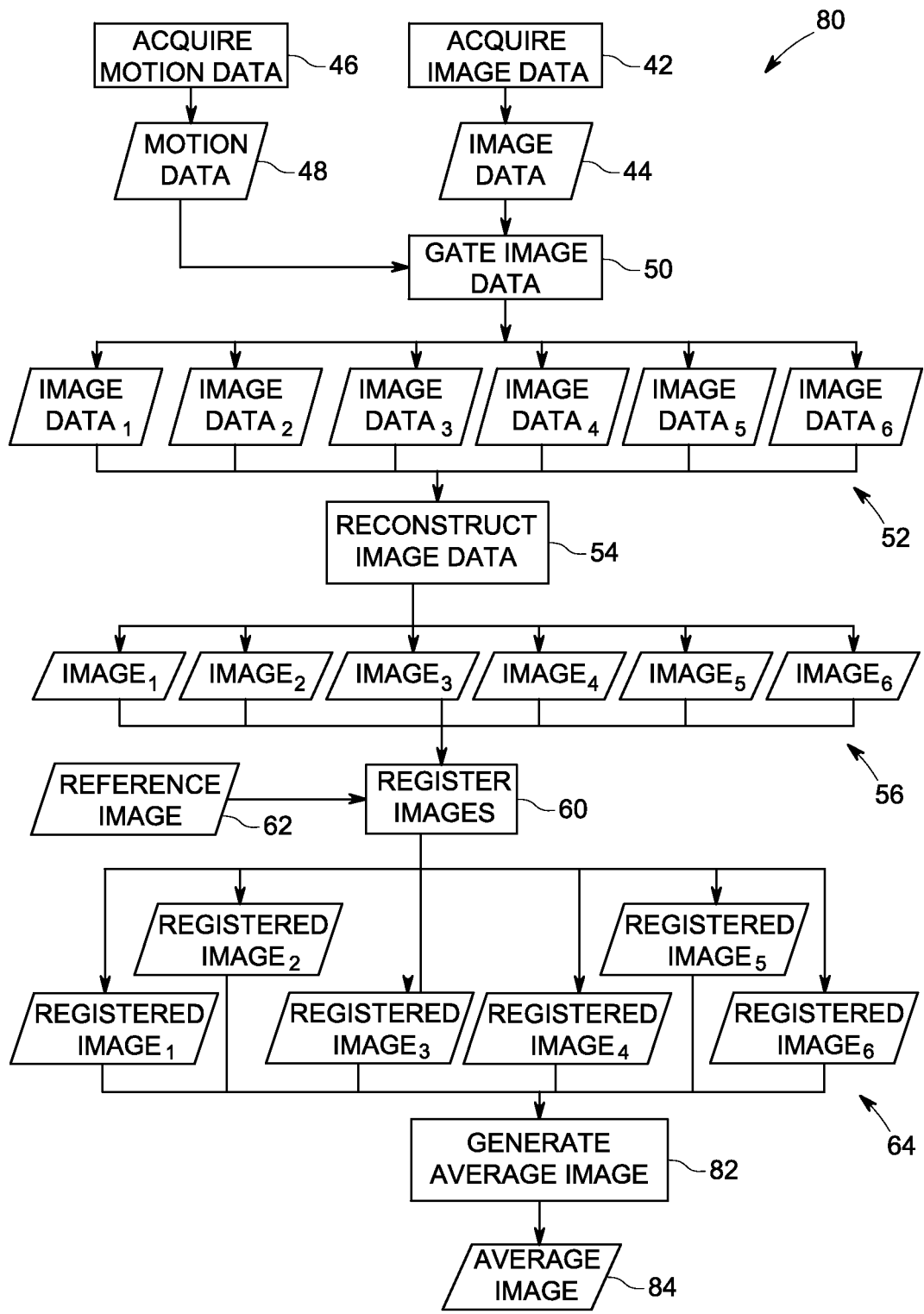
FIG. 3 is a flowchart depicting a method for image processing used to generate an average image in accordance with one embodiment of the present disclosure.

Turning to FIG. 3, in another embodiment a method 80 is depicted in which the registered images 64 are averaged (block 82) to generate an average image 84. For example, in an embodiment in which an averaging process is employed, the average image 84 may be obtained by computing the average over gates (at every voxel) in accordance with:

$$I_v^{Mean} = \frac{1}{N}\sum_{g=1}^{N} r_{gv} \quad (2)$$

where $I_v^{Median}$ is the average image, $r_g$, corresponds to the voxel value for a given voxel in a given registered image, N is the number of gates, g is the gate index, and v is the voxel index. The average image 84 may be viewed by trained personnel for evaluation.

Figure 4:
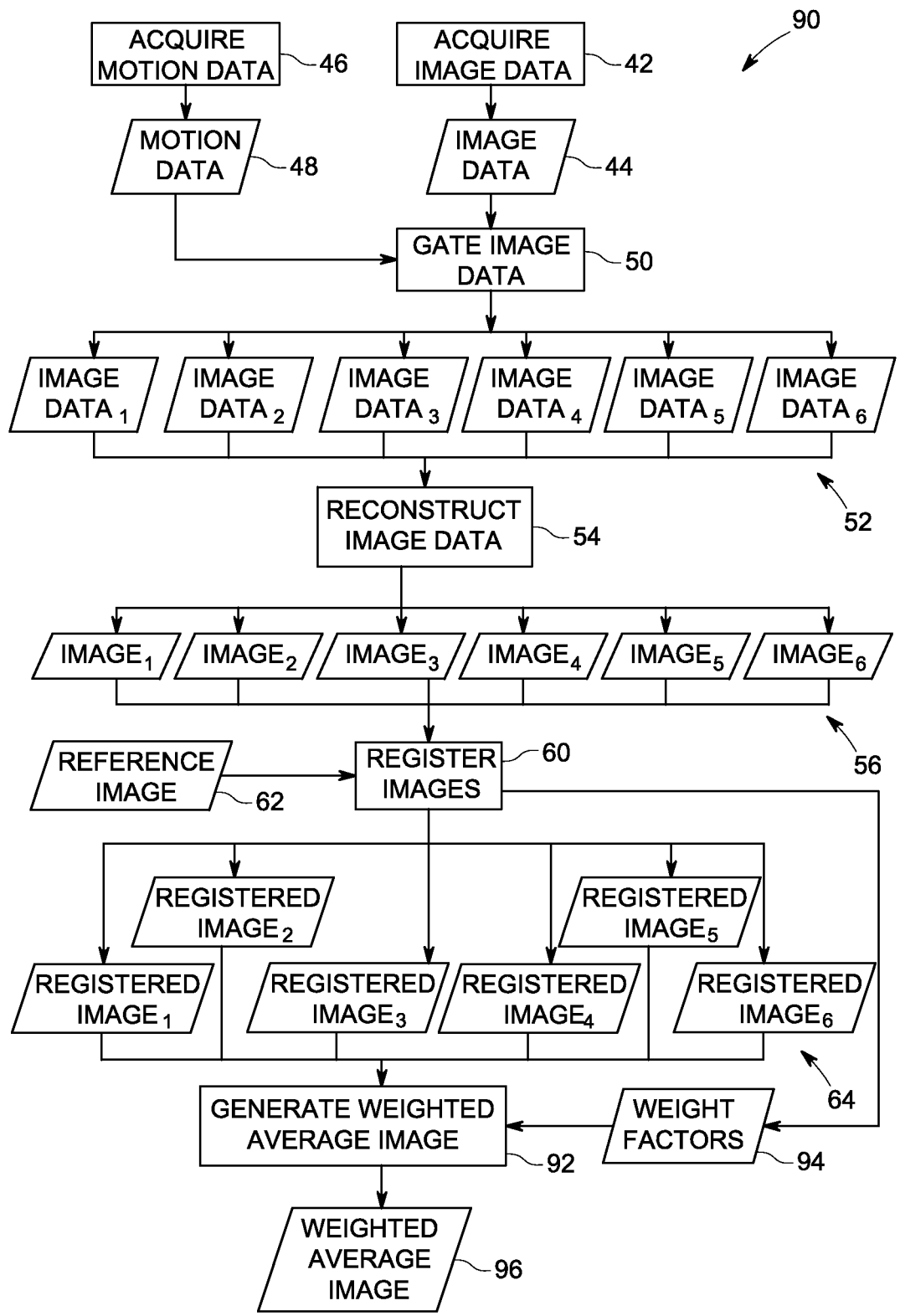
FIG. 4 is a flowchart depicting a method for image processing used to generate a weighted average image in accordance with one embodiment of the present disclosure.

Alternatively, turning to FIG. 4, in a further embodiment, a method 90 is depicted in which the registered images 64 undergo a weighted average operation (block 92) to generate a weighted average image 96. The weight factors 94 employed in the depicted embodiment are generated based on information derived from the registration process (e.g., motion estimates, transformation vectors, and so forth) that may be used to provide some estimate of confidence, or lack of confidence, in individual voxels or regions of voxels within the registered images 64 being weighted. In one implementation, the weighted average image 96 may be derived in accordance with:

$$I_v^{Wt'd\_Mean} = \sum_{g=1}^{N} w_{gv} r_{gv} / \sum_{g=1}^{N} w_{gv} \quad (3)$$

where $I_v^{Wt'd\_Median}$ is the weighted average image, g is the gate index; v denotes a respective voxel position or voxel index within the images; $w_{gv}$ corresponds to the weighting factor for a given voxel in a given registered, gated image; and $r_{gv}$ corresponds to the voxel value for a given voxel in a given registered image. In one implementation, the weighting factors, w, are based on an estimate of the success of the registration locally, though other weighting schemes may also be employed.

With respect to the weighting schemes that may be employed, in one embodiment, the weight factors 94 may be based on motion analysis, as determined from the registration process. For example, in one such embodiment the registered images $r_g$ are obtained by interpolating the original gated images $I_g$ on the deformed grid $D_g$, where $D_g$ is the estimated deformation field (giving a 3D vector in every voxel, specifying where the voxel is located in the reference image). In such an implementation, the weight factors, w, in equation (3) may be determined based on an estimate of how well the registration succeeded (locally). Different metrics may be used to determine the weights $w_{gv}$. For example, if the estimated deformation in a voxel/gate is too large according to prior knowledge, its weight may be set to zero, e.g.:

$$w_{gv}^{size} = \begin{cases} 1 & \text{if } \|D_{gv}\| < 4\,\text{cm} \\ 0 & \text{otherwise} \end{cases} \quad (4)$$

In addition, in one implementation the determinant J of the 3×3 Jacobian matrix of the deformation field may be used as a metric. For a continuous deformation field D, the Jacobian may be computed as $$J = \det\left(\frac{\partial D_i}{\partial x_j}\right) \quad (5)$$

with i and j running from 1 to 3. In one implementation, the Jacobian J may be computed using $1^{st}$ order differences of the discretized deformation fields $D_g$. If $J_g$, is negative, it indicates a non-invertible transformation, and the corresponding weight may be set to zero. Further, very large Jacobians may indicate large expansions or motions, which could be indicative of a physically unlikely (or impossible) occurrence in a medical image context. One simple weighting scheme may, therefore, be as follows:

$$w_{gv}^J = \begin{cases} 1 & \text{if } 0 < J_{gv} < 5 \\ 0 & \text{otherwise} \end{cases} \quad (6)$$

In the case of very large motion such that there is no overlap between a feature in a gate and the reference gate, a registration algorithm may erroneously return a small deformation (presumably because it is trapped in a local minimum). This case may go undetected in the preceding weighting schemes. Therefore in one implementation, a metric may be included which checks if the image values are close after registration. For instance when using a reference gate $g_0$, such a check may be performed in accordance with:

$$w_{gv}^{val} = \exp(-(r_{gv} - I_{gv})^2 / 2\sigma^2) \quad (7)$$

where σ is determined from known noise factors or allowable image differences. In practice, the above weights may be computed on smoothed images to reduce the influence of noise.

In addition, weights based on external information about the scan or gate may be employed. In one example, the DICOM header of the images normally contains information about the estimated scatter fraction. For most PET applications, it is expected that this scatter fraction is reasonably similar for the different gates. Therefore, a useful confidence measure would be given by a decreasing function of the difference between the scatter fractions with e.g. the reference gate, or a population based measure.

In one embodiment, a set of final weights may be determined based on product of two or more of the above weighting approaches, such as:

$$w_{gv} = w_{gv}^{size} w_{gv}^J w_{gv}^{val} \quad (8)$$

In one implementation, one of the gated images 56 may serve as a reference gate for the remaining gated images in the image registration process. In such an embodiment, the deformation field for the reference gate is thus, by assumption, perfect and all weights for the reference gate may be set to 1. This insures that every voxel always has at least one gate contributing to the weighted average image 96.

It should be appreciated that other methods to find appropriate weighting factors can be useful. Examples of such approaches are discussed in U.S. patent application Ser. No. 12/873,039, entitled "MOTION COMPENSATION IN IMAGE PROCESSING", filed Aug. 31, 2010, which is incorporated by reference in its entirety for all purposes.

Figure 5:
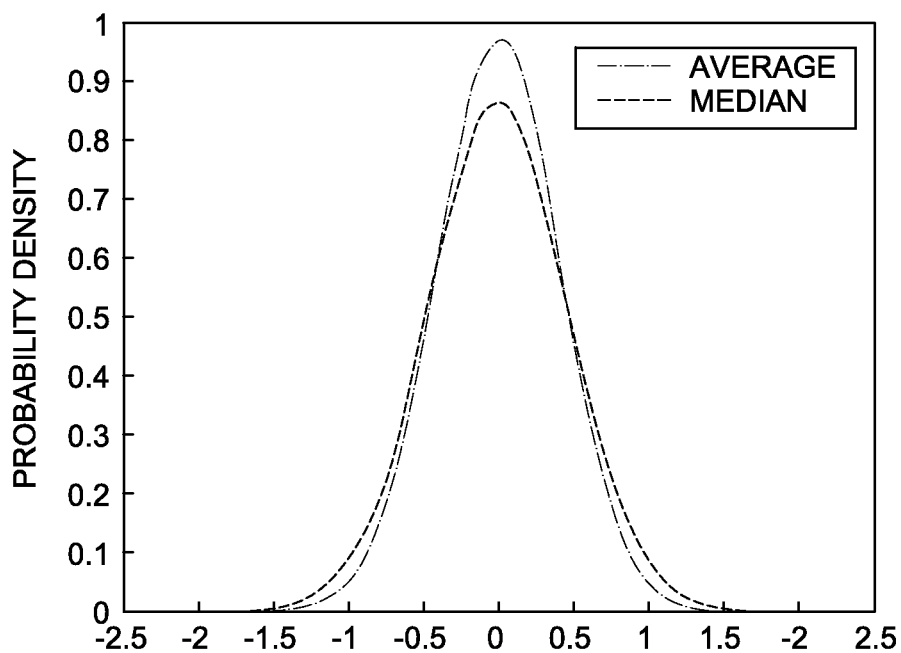
FIG. 5 depicts probability density functions describing median and average values derived using simulated data.

With the foregoing discussion of the calculation and use of median images, 70, average images 84, and weighted average images 96 in mind, the following statistically simulated comparison is provided to illustrate the relative merits of these different approaches. In one such comparison a Monte Carlo approach was used to obtain average and median values from 1,800,000 runs of sampled data sorted (i.e., binned) into 6 gates wherein the data points are generated based upon a standard normal distribution (i.e., mean of 0 and a standard deviation of 1). This simulation is comparable to studying a single voxel that is spatially uncorrelated with other voxels. The probability density functions of the average and median values are depicted in FIG. 5. In this simulation, both the average and median estimators are unbiased but the median has a slightly wider distribution, as depicted in FIG. 5.

Figure 6:
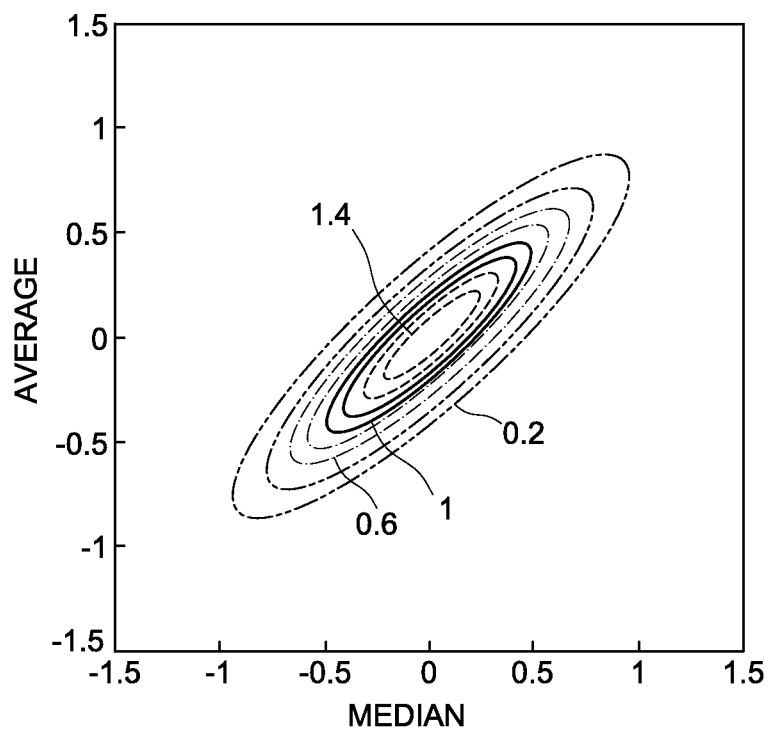
FIG. 6 depicts a joint distribution function of the median and average values of FIG. 5.

The joint distribution for the simulated dataset is depicted in FIG. 6. As depicted in FIG. 6, the distribution is concentrated almost along the diagonal. This essentially means that the average and the median estimate are not apart from each other (when there are no outliers). Thus, in the absence of outlying data points, the average and median estimators perform comparably.

Figure 7:
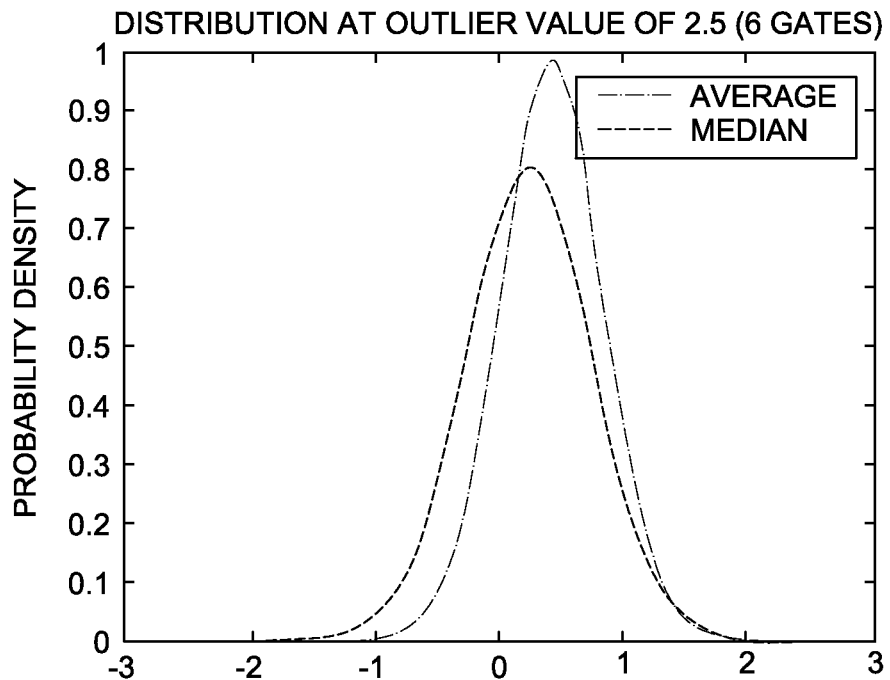
FIG. 7 depicts probability density functions describing median and average values derived using simulated data that includes simulated outliers.
Figure 8:
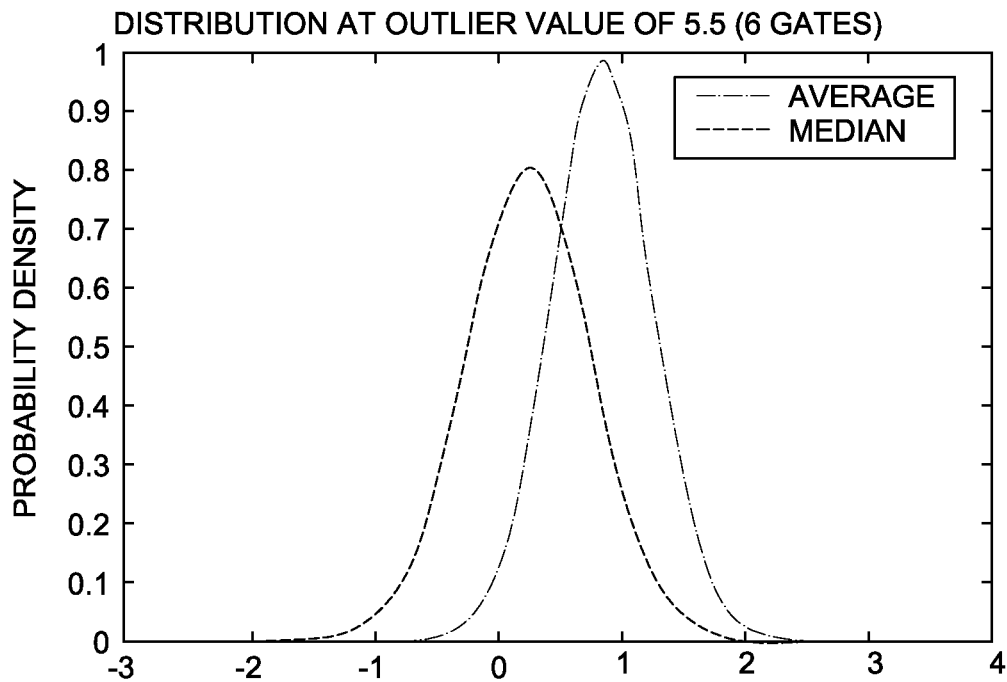
FIG. 8 depicts another probability density functions describing median and average values derived using simulated data that includes simulated outliers.

While FIGS. 5 and 6 depict the probability density and joint distribution functions where there is no outlying data between the respective gates, FIGS. 7 and 8 depict probability density functions where an outlying data set (i.e., gate) is simulated. In particular, FIGS. 7 and 8 are based on simulated data obtained from 1,800,000 runs of 6 sample data gates with 1 outlier gate. All samples are based on a normal distribution with the same standard deviation of 1. FIG. 7 depicts a simulation in which five of the sample sets have a mean of 0 while one sample set has a mean of 2.5. FIG. 8 depicts a simulation in which five of the sample sets have a mean of 0 while one sample set has a mean of 5.5. As depicted in FIGS. 7 and 8, the median estimator remains relatively unbiased while the average estimator has a mean that is biased toward the outlying data.

In view of the simulated studies noted above as well as clinical studies in which the use of average images 84 and median images 70 were compared, it is believed that the use of median images 70 helps mitigate artifacts attributable to the registration process and increases the robustness of the final estimate.

With the foregoing discussion of generating an average image 84 or weighted average image 96 in mind, it may be appreciated that statistically characterizing the errors introduced by the registration step 60 may be difficult. This in turn may impact the estimation of the true pixel value based on a given number of data measurements and a given number of gates (e.g., six). It may therefore be useful to employ methods for estimating the true pixel value that are more robust to the presence of outliers. Estimating the average or weighted average over registered gates, as discussed above, is equivalent to using a (weighted) least squares cost function as:

$$E_v(x) = \sum_{g=1}^{N} w_{gv} \{r_{gv} - x\}^2 \quad (9)$$

where the estimate for the true value of the image at voxel index v is obtained by minimization the cost function over x.

However, in other embodiments the estimator employed is not a least squares estimator and is instead an estimator that is robust in the event of outliers that are attributable to random outlier noise along with a regular "Gaussian" error introduced by the registration process. In such an embodiment, the cost function employed is suitable for use even in instances where there are only a few samples (e.g., ten or fewer gates, such as six gates) to robustly estimate the data. There are two different approaches to reduce the influence of outliers. In certain embodiments, the cost function is adapted to downweight outliers without explicit identification, while in other embodiments, outliers may be explicitly identified and rejected during the estimation process.

There are a variety of cost functions that may be employed to reduce the effect of outliers without explicit identification and which may be suitable in estimating an average image or a weighted average image. In an estimation problem, assuming that there are N observations $y_i$ and x is the parameter to be estimated, a cost function may typically be defined as follows:

$$C(x) = \sum_{i=1}^{N} \rho(y_i - x) \quad (10)$$

where p is the loss function and the estimate is obtained by minimizing the cost function over x. Such estimators are generally called M-estimators.

One example of an estimator that may be employed to estimate an average or weighted average image is the Huber loss function, which is defined as:

$$\rho_C(\varepsilon) = \begin{cases} \dfrac{\varepsilon^2}{2}, & |\varepsilon| \le C \\ C\left(|\varepsilon| - \dfrac{\varepsilon}{2}\right), & |\varepsilon| > C \end{cases} \quad (11)$$

Figure 9:
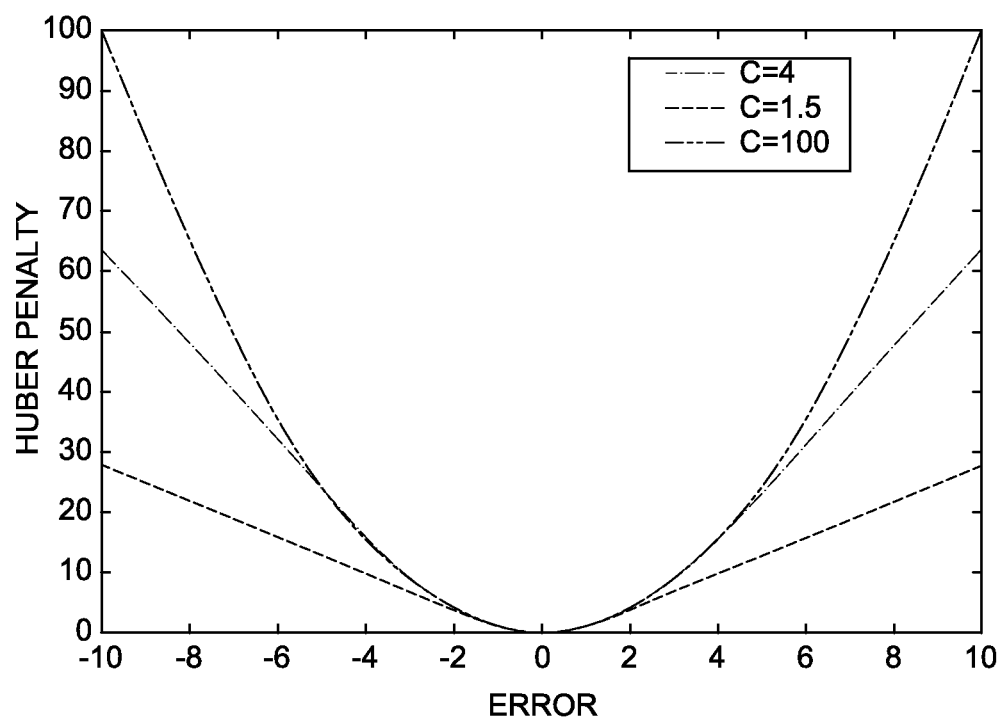
FIG. 9 depicts an example of one suitable cost function for generating average or weighted average images in accordance with the present disclosure.

From the above equation it can be seen that the Huber loss function alternates between the quadratic and non-quadratic behavior. In particular, the Huber loss function is quadratic when $|\varepsilon|$ is less than C and it rises linearly with $|\varepsilon|$ otherwise. Indeed, as C tends to 0, the loss function yields a median estimator whereas setting it to a very large value would lead to the average, i.e., mean value. Plots of the Huber cost for different values of $\varepsilon$ and three different values of C are shown in FIG. 9.

In an estimation problem, assuming that there are N observations $y_i$ and x is the parameter to be estimated, the Huber loss function is used as follows:

$$E(x) = \sum_{i=1}^{N} \rho_C\left\{\frac{y_i - x}{\sigma}\right\} \quad (12)$$

where the minimization is done over x.

With respect to the respective parameters of equation 12, the parameter $\sigma$ can be considered a kind of scaling constant for normalizing the error across observations. Although in the above expression, this is assumed to be constant for all data points, this need not be so. In the most general case, this parameter can also vary with the sample points. This is called the heteroscedasticity; where the conditional variance changes with the observation. The values for $\sigma$ can be either known a priori from the measurement process or estimated from data itself, such as using the sample standard deviation or the median absolute deviation. For estimating the pixel value across the registered gates, it may be useful to vary a based on an independent factor. The Jacobian of the motion field, for instance, is a good source of the correctness or accuracy of the registration. While mis-registration is reflected in the value of the pixel as well, the Jacobian provides additional information. For example, as discussed above, very large and small values of the Jacobian indicate that the deformation in the region is not normal. Such metrics may also use external tracker information for instance to reject gates with large intra-gate motion, or to prefer gates which are close to a quiescent phase.

Given the relation between a weighted average and a weighted least squares estimator noted above, it is possible to use:

$$\sigma_{gv} = \frac{1}{\sqrt{w_{gv}}} \quad (13)$$

in a suitable weighting scheme.

The parameter C in the Huber function controls the effect of the data points. The data points which differ froth the current estimate by a value greater than C times $\sigma$ have a smaller influence on the total cost and vice versa. The parameter for the Huber cost function is the cutoff factor. It can be seen that if this is a sufficiently high number, the estimation is equal to a least squares estimation for which the minimizer is the sample mean. On the other hand, if C=0, then it can be shown that the estimator minimises the absolute difference of the error rather than the squared error. The cutoff parameter decides, in some sense, which points are to be given low weights. In other words, this parameter decides which are the outliers and rejects them. Assuming that the data follows the normal distribution, a value of C=1.345 gives 95% efficiency.

Other outlier robust objective functions may have similar parameters. In general, such functions will include some estimate of the expected variation and some threshold. In the case of the Huber loss function, the final estimate only depends on C times $\sigma$, therefore "independent" factors about known image or registration quality can be incorporated into one or both of C or $\sigma$. For other objective functions, it might be more suitable to maintain $\sigma$ as an expected variance in the data given good registration quality, and change the "threshold" parameters based on estimated registration quality such that voxels in gates with low registration quality are considered outliers. While in some embodiments the parameters of the objective function are determined beforehand (i.e. variances and thresholds that are established before performing the optimization), in other embodiments the weights may instead be based on the current estimate, with the estimation process being iterated or restarted until a completion criterion is satisfied.

While the preceding discussion focuses on implementations based on the Huber loss function, in an alternative approach outlier/non-outlier gates can be explicitly classified at each pixel. An embodiment of one such approach uses the RANSAC method. In an alternative embodiment, given N data points (corresponding to N gate data at each voxel), the variance of the non-outlier data is within observed variance trends in a neighborhood of the voxel. To avoid trivial solutions where small groups of data meeting the variance bound are picked, a penalty may be enforced for the size of the outlier group. Thus at each voxel, an optimization problem is solved to group the input data to outlier/non-outlier clusters and finally output the mean of the non-outlier data.

In one such approach, given N data points (e.g., N of 6) at each voxel, a binary indicator function $w_g$ at $g=1, 2, \ldots N$ may be found. For example, $w_g=0/1$ indicates an outlier/non-outlier data point at g. Let $\text{Var}_{NO}$ denote variance computed over the non-outlier set $\{w_g I_g\}_{g=1}^{N}$. The following energy E is minimized over the indicator function $w_g$ and the mean over the non-outlier group, µ. That is, the equation:

$$E[w, \mu] = \sum_g (1 - w_g) \tag{14}$$

is minimized such that:

$$w_g \in \{0,1\} \tag{15}$$

And such that:

$$Var_{NO} = \frac{\sum_g w_g[(I_g - \mu)^2]}{\sum_g w_g} \leq \sigma^2. \tag{16}$$

In one such embodiment, an update of µ may be given as:

$$\mu = \frac{\sum_g w_g I_g}{\sum_g w_g}. \tag{17}$$

In one such implementation, the energy minimizes the size of the outlier group while imposing the two constraints. The first constraint being that $w_g$ is binary and the second constraint bounds the variance in the non-outlier group by $\sigma^2$. Since the indicator function is binary, it is easy to minimize the above energy when N is small. In one approach, the initial number of outliers would be set at 0 and would be subsequently increased, stopping when a combination in the non-outlier group meets the variance bound. This scheme has a worst-case complexity $O(N2^N)$ which is prohibitive for large N but feasible for smaller values of N, such as an N value of 6. Another possibility is to use a gradient descent type iterative scheme for the above problem and minimize over continuous values of $w_g$. Such an approach would be faster for large N and would also accommodate non-binary $w_g$. Further, in certain scenarios, it may be useful to preserve the original data and to not completely discard some of it as outliers. In such scenarios, a fuzzy/soft version of $w_g$ taking continuous values may be appropriate.

In yet another approach, registration or original data quality may be estimated or evaluated and used as a constraint on the generation of an average image or a weighted average image. For example, in a PET imaging context the registration step may be affected due to scatter induced intensity variations and large motion leading to unrealistic motion estimates as discussed before. Thus it may be useful to change cost function to leave out pixels from gates that are potentially unreliable due to inaccurate registration. One measure of reliability discussed herein is the Jacobian of the motion vector field output by registration, which captures the degree of contraction/expansion and anomalies, such as crossovers and tears (which do not occur in most anatomical structures). Thus, to leave out data points that appear to be associated with physically infeasible locations, Jacobian based constraints may be added to or otherwise incorporated with the above energy.

For example, one could simply bound the Jacobian at a non-outlier voxel to lie within reasonable bounds, such as by adding the constraint:

$$w_g W_{\alpha,\beta}(J_g) = 0 \tag{18}$$

to the minimization problem, where $J_g$ is the Jacobian of the motion vector field at the current voxel of the $g^{th}$ gate. The motion vector field is the output of registering the $g^{th}$ gate with the reference gate. $W_{\alpha,\beta}(x)$ is a binary ID function that takes a value 1 when x lies outside feasible deformation bounds $[\alpha,\beta]$. Thus, when $W_{\alpha,\beta}(J_g)=1$ the constraint forces $w_g=0$. Alternatively, in the case of a non-binary $w_g$, the left expression in Equation (18) can be added as a penalty to the energy (equation 14) with a continuous version of $W_{\alpha,\beta}(x)$ so that partial information from a gate with large deformation is still used. As will be appreciated, other registration quality measures can be employed in the same way.

One aspect of certain of the preceding approaches is the estimation of the normalcy of the data signified by the variance bound $\sigma^2$. In PET data, where the data statistics are Poisson like, it may be observed that data standard deviation is spatially varying. So a may be tuned at each voxel. One way to pick σ is as follows. First, a set of correlated voxels (i.e. with possibly similar σ) to the current voxel is picked. Next, among the correlated pixels, pick those with minimum registration induced errors. The mean of the standard deviation is taken over gates at down selected voxels.

If the data is close to being Poisson distributed, a would be characterized by image intensity. Thus, the reference gate may be considered (since it is the original data, uncorrupted by registration errors) and intensity may be compared in a neighbourhood around the current voxel (e.g., a neighborhood of (10×10×5). The voxels with intensity within a threshold of the current voxel intensity are picked as correlated voxels.

Within these correlated voxels, a from gate data least corrupted by registration errors is determined. One approach for making this determination is to look at voxels with motion vectors close to zero. Such a scenario is possible in homogeneous regions where there are no gradients to drive the registration algorithm. In these cases there is a possibility of over estimating σ since noisy voxels that are not registered to the correct location influence the statistics. Alternatively, any suitable registration quality measure can be used to select the voxels (i.e. only pick voxels where the registration quality measure is high). Examples of many such suitable measures are discussed herein, and in the incorporated reference.

In addition, in certain embodiments, patch-based extensions may be employed. For example, in the case of data with large standard deviation across gates, it might be difficult to find an appropriate bound $\sigma^2$ to distinguish outliers and non-outliers. Another criterion for rejecting outliers is to measure patch-wise correlations at current voxel across the original gated data. The idea is to use the output motion vector at the current voxel and trace back to the original data. Then patch wise correlations would measure registration accuracy in a larger neighborhood. For example, such an approach would rule out cases where shape of structures have been dramatically distorted to match intensity, since a patch wise match pre-supposes locally rigid deformations only and hence a good match of image geometry. In addition, in noisy, low contrast regions, registration mismatch may be more easily determined with patch based metrics rather than voxel based metrics. A patch based extension to equation (16) is to modify the Variance bound condition to:

$$\frac{\sum_g w_g \frac{1}{|P_x|} \int_{P_x} (I_g(y + (D_{gx} - x)) - \mu(y))^2 dy}{\sum_g w_g} \leq \sigma_P^2 \quad (19)$$

where $P_x$ is a patch around voxel x, $D_{gx}$ is the transformation at x for gate g $\sigma_p^2$ is a bound that is learned from the data. The patch size is a parameter that depends on the amount of non-rigid variability present around the current voxel. Structures with large non-rigid deformations would require a smaller patch size. One possibility is to look at the motion estimates at the current voxel across gates and infer the patch size approximately from them. The integral in equation (19) attributes the same weight to all voxels in the patch. In another embodiment, the integral is modified with a weight function that decreases to zero for voxels at the edge of the patch. In addition, registration quality measures can be incorporated using penalties as before.

Technical effects of embodiments of the present invention include using a suitably configured circuit or processor to calculate a median image generated based upon a number of registered gated images. Other technical effects may include calculation of an average image or weighted average image based upon a number of registered gated images and using a cost function that is robust with respect to outlying data values. Another possible technical effect may include the explicit identification of outlying data values and the exclusion of such outlying data values in the calculation of an average image or weighted average image.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for generating an image, comprising:
acquiring a first set of image data using a first imaging modality;
sorting the first set of image data into a plurality of gates to generate a plurality of gated data sets;
reconstructing each gated data set to generate a respective gated image for each gated data set;
registering the respective gated images to generate a plurality of registered images; and
generating a median image from the plurality of registered images, wherein each voxel of the median image is a respective median value of the corresponding voxels of the plurality of registered images.

2. The method of claim 1, wherein the first imaging modality is one of positron emission tomography (PET) or single photon emission computed tomography (SPECT).

3. The method of claim 1, wherein the plurality of gates comprises a predetermined number of gates.

4. The method of claim 1, wherein the first set of image data is sorted into the plurality of gates based on at least one of time and motion.

5. The method of claim 1, wherein the respective gated images are registered based on a motion field determined from a secondary registration performed on a second image dataset acquired using a second imaging modality.

6. The method of claim 1, wherein the respective gated images are registered based on measured cardiac or respiratory motion data.

7. One or more non-transitory computer-readable media, encoding one or more routines which, when executed by a processor, cause the processor to perform acts comprising:
acquiring a first set of image data using a first imaging modality;
sorting the first set of image data into a plurality of gates to generate a plurality of gated data sets;
reconstructing each gated data set to generate a respective gated image for each gated data set;
registering the respective gated images to generate a plurality of registered images; and
generating a median image from the plurality of registered images, wherein each voxel of the median image is a respective median value of the corresponding voxels of the plurality of registered images.

8. The one or more non-transitory computer-readable media of claim 7, wherein the first imaging modality is one of positron emission tomography (PET) or single photon emission computed tomography (SPECT).

9. The one or more non-transitory computer-readable media of claim 7, wherein the plurality of gates comprises a predetermined number of gates.

10. The one or more non-transitory computer-readable media of claim 7, wherein the first set of image data is sorted into the plurality of gates based on at least one of time and motion.

11. The one or more non-transitory computer-readable media of claim 7, wherein the respective gated images are registered based on a motion field determined from a secondary registration performed on a second image dataset acquired using a second imaging modality.

12. The one or more non-transitory computer-readable media of claim 7, wherein the respective gated images are registered based on measured cardiac or respiratory motion data.

13. An image processing system, comprising:
a memory storing one or more routines, and
a processing component configured to execute the one or more routines stored in the memory, wherein the one or more routines, when executed by the processing component:
acquire a first set of image data using a first imaging modality;
sort the first set of image data into a plurality of gates to generate a plurality of gated data sets;
reconstruct each gated data set to generate a respective gated image for each gated data set;
register the respective gated images to generate a plurality of registered images; and
generate a median image from the plurality of registered images, wherein each voxel of the median image is a respective median value of the corresponding voxels of the plurality of registered images.

14. The image processing system of claim 13, wherein the first imaging modality is one of positron emission tomography (PET) or single photon emission computed tomography (SPECT).

15. The image processing system of claim 13, wherein the plurality of gates comprises a predetermined number of gates.

16. The image processing system of claim 13, wherein the first set of image data is sorted into the plurality of gates based on at least one of time and motion.

17. The image processing system of claim 13, wherein the respective gated images are registered based on a motion field determined from a secondary registration performed on a second image dataset acquired using a second imaging modality.

18. The image processing system of claim 13, wherein the respective gated images are registered based on measured cardiac or respiratory motion data.

19. A method for generating an image, comprising:
acquiring a first set of image data using an imaging modality;
sorting the first set of image data into a plurality of gates to generate a plurality of gated data sets;
reconstructing each gated data set to generate a respective gated image for each gated data set;
registering the respective gated images to generate a plurality of registered images; and
generating an average image or a weighted average image from the plurality of registered images, wherein the average image or the weighted average image is generated using a motion-dependent estimator that is statistically robust with respect to outlying data.

20. A method for generating an image, comprising:
acquiring a first set of image data using an imaging modality;
sorting the first set of image data into a plurality of gates to generate a plurality of gated data sets;
reconstructing each gated data set to generate a respective gated image for each gated data set;
registering the respective gated images to generate a plurality of registered images; and
generating an average image or a weighted average image from the plurality of registered images, wherein the average image or the weighted average image is generated using an estimator that identifies outliers in the plurality of registered images and discards or down-weights the identified outliers.

* * * * *

UNITED STATES PATENT AND TRADEMARK OFFICE
CERTIFICATE OF CORRECTION

PATENT NO. : 8,569,706 B2
APPLICATION NO. : 13/487046
DATED : October 29, 2013
INVENTOR(S) : Thiruvenkadam et al.

It is certified that error appears in the above-identified patent and that said Letters Patent is hereby corrected as shown below:

On the Title Page, in Item (75), in Column 1, Line 5, delete "Kamataka" and insert -- Karnataka --, therefor.

On the Title Page, in Item (56), under "OTHER PUBLICATIONS", in Column 2, Line 1, delete "resiratory" and insert -- respiratory --, therefor.

On the Title Page, in Item (56), under "OTHER PUBLICATIONS", in Column 2, Line 7, delete "Position" and insert -- Positron --, therefor.

In the Drawing:

In Fig. 5, Sheet 5 of 7, delete "  " and insert -- -- , therefor.

In the Specification:

In Column 4, Lines 31-32, delete "detector acquisition circuitry 14," and insert -- data acquisition circuitry 14, -- therefor.

In Column 5, Line 31, delete "detector acquisition circuitry 14" and insert -- data acquisition circuitry 14 --, therefor.

In Column 5, Line 34, delete "detector acquisition circuitry 14" and insert -- data acquisition circuitry 14 --, therefor.

In Column 7, Line 44, in Equation (1), delete " $I_v^{Median} = \text{median}(r_{1v}, r_{2v}, \ldots, t_{Nv})$ "

and insert -- $I_v^{Median} = \text{median}(r_{1v}, r_{2v}, \ldots, r_{Nv})$ --, therefor.

Signed and Sealed this
Twenty-fifth Day of February, 2014

Michelle K. Lee
*Deputy Director of the United States Patent and Trademark Office*

CERTIFICATE OF CORRECTION (continued)
U.S. Pat. No. 8,569,706 B2

In Column 8, Line 7, delete "$I_v^{Median}$ is the average image, $r_g$," and insert -- $I_v^{Mean}$ is the average image, $r_{gv}$ --, therefor.

In Column 8, Line 32, delete "$I_v^{wt'd\_Median}$" and insert -- $I_v^{wt'd\_Mean}$ --, therefor.

In Column 9, Line 8, delete "$J_g$," and insert -- $J_{gv}$ --, therefor.

In Column 11, Line 19, delete "p" and insert -- $\rho$ --, therefor.

In Column 12, Line 18, delete "froth" and insert -- from --, therefor.

In Column 12, Line 19, delete "a" and insert -- $\sigma$ --, therefor.

In Column 14, Line 4, delete "ID" and insert -- 1D --, therefor.

In Column 14, Line 18, delete "a" and insert -- $\sigma$ --, therefor.

In Column 14, Line 25, delete "a" and insert -- $\sigma$ --, therefor.

In Column 14, Line 30, delete "(10×10×5)." and insert -- (10×10×5)). --, therefor.

In Column 15, Line 9, delete "$g\sigma_p^2$" and insert -- $g$ and $\sigma_p^2$ --, therefor.